(12) United States Patent
Sperl

(10) Patent No.: US 8,262,636 B2
(45) Date of Patent: Sep. 11, 2012

(54) DISPOSABLE ABSORBENT ARTICLE WITH DONNING TAB

(75) Inventor: Michael Donald Sperl, Waupaca, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 12/910,352

(22) Filed: Oct. 22, 2010

(65) Prior Publication Data

US 2012/0101463 A1 Apr. 26, 2012

(51) Int. Cl.
*A61F 13/15* (2006.01)

(52) U.S. Cl. ........ 604/386; 604/387; 604/389; 604/390; 604/391

(58) Field of Classification Search .................. 604/387, 604/389, 390, 391
See application file for complete search history.

(56) References Cited

U.S. PATENT DOCUMENTS

| | | | |
|---|---|---|---|
| 5,204,997 | A | 4/1993 | Suzuki et al. |
| 5,531,732 | A | 7/1996 | Wood |
| 5,624,429 | A | 4/1997 | Long et al. |
| 6,210,386 | B1 | 4/2001 | Inoue |
| 6,213,991 | B1 | 4/2001 | Kling et al. |
| 6,475,205 | B2 | 11/2002 | Shimada et al. |
| 6,503,239 | B1 * | 1/2003 | Bruemmer-Prestley et al. ......................... 604/385.29 |
| 6,746,433 | B1 | 6/2004 | Shimoe et al. |
| 7,156,834 | B2 | 1/2007 | Kawata et al. |
| 7,198,621 | B2 * | 4/2007 | Moser et al. ............. 604/385.22 |
| 7,255,688 | B2 | 8/2007 | Sasaki et al. |
| 2003/0055394 | A1 | 3/2003 | Gibbs |
| 2005/0175269 | A1 | 8/2005 | Ashton et al. |
| 2008/0108963 | A1 | 5/2008 | Ashton et al. |
| 2010/0004616 | A1 * | 1/2010 | Nakamura et al. ............ 604/389 |
| 2011/0178485 | A1 * | 7/2011 | LaVon et al. .................. 604/365 |

FOREIGN PATENT DOCUMENTS

| | | |
|---|---|---|
| JP | 11-104180 A | 4/1999 |
| JP | 04-020340 B2 | 10/2007 |
| WO | WO98/13002 | 4/1998 |
| WO | WO2007/073247 | 6/2007 |

* cited by examiner

*Primary Examiner* — Lynne Anderson
*Assistant Examiner* — Bradley Philips
(74) *Attorney, Agent, or Firm* — Randall W. Fieldhack

(57) ABSTRACT

An absorbent article includes front and back side panels, wherein each side panel has an attachment edge and a free edge, the front and back side panels being one of permanently attached and releasably fastenable to define a wear configuration of the absorbent article. The article also includes a finger tab system including a finger tab having first and second ends and a distal point, the first end of the finger tab being attached to the free edge of one of the front and back side panels, and a tab line where the finger tab intersects the free edge of the one of the front and back side panels, wherein the finger tab system includes an aperture disposed between the distal point of the finger tab and the tab line.

15 Claims, 8 Drawing Sheets

DISPOSABLE ABSORBENT ARTICLE WITH DONNING TAB

BACKGROUND

The present disclosure relates generally to absorbent articles intended for personal wear, and more particularly to disposable absorbent articles.

Many absorbent articles intended for personal wear, e.g., such as diapers, training pants, feminine hygiene products, adult incontinence products, bandages, medical garments and the like are designed to be sufficiently absorbent to pull moisture from liquid body exudates including urine, menses, blood, etc. away from the wearer to reduce skin irritation caused by prolonged wetness exposure. Diapers, as an example, are typically placed and secured on a wearer using a set of primary fastening tabs, such as adhesive tabs or mechanical (e.g., hook or loop) fastening system tabs and left in place to absorb insults as well as to contain fecal waste. When the diaper is to be disposed of, the caregiver will sometimes fold the diaper into a more compact configuration and secure the diaper in this configuration using the primary fastening tabs.

Training pants, unlike diapers, typically come pre-assembled in a wear configuration to more closely resemble conventional underpants. In particular, front and back waist regions of such training pants are typically fastened at a seam either permanently or refastenably (such as by a primary fastening system) to define a wear configuration of the pants having a waist opening and leg openings. Training pants that are designed to fit snugly around the waist and hips of the wearer can sometimes be difficult for a wearer or caregiver to raise over the hips. Toddlers have limited dexterity and grasping power. The side panel and chassis itself are generally flexible and thin with no handles to facilitate a means to grip the training pants.

SUMMARY

There is a need, therefore, for a finger tab system provided on an absorbent article such as training pants for improved donning ability. Disclosed herein is a pant design that increases the ease of donning a training pant by providing wearers and caregivers with an improved finger/hand grasping mechanism. This enables toddlers, for example, to successfully don the pant at an earlier date. The improved grasping also allows toddlers to pull up pants with a decreased waist opening, tighter waist opening, and or greater pant to skin friction that can facilitate expanding current training pant size ranges or achieving better gasketing performance. The pant design also provides a sufficient visual awareness to the consumer of the presence of such a fastening system and sufficient operability and use of such a fastening system.

In one aspect, an absorbent article for personal wear about a wearer's waist includes a liquid permeable inner surface for facing the wearer, an outer surface for facing away from the wearer, an absorbent body disposed therebetween, and a front waist region, a back waist region, and a crotch region extending longitudinally between and interconnecting the front and back waist regions. The article also includes a front side panel attached to the front waist region and a back side panel attached to the back waist region, wherein each side panel has an attachment edge and a free edge, the front and back side panels being one of permanently attached and releasably fastenable to define a wear configuration of the absorbent article having a waist opening and a leg opening spaced from the waist opening, wherein the front and back side panels each extend from the waist opening to the leg opening. The article also includes a finger tab system including a finger tab having first and second ends and a distal point, the first end of the finger tab being attached to the free edge of one of the front and back side panels, and a tab line where the finger tab intersects the free edge of the one of the front and back side panels, wherein the finger tab system includes an aperture disposed between the distal point of the finger tab and the tab line.

In another aspect, absorbent article for personal wear about a wearer's waist, has a transverse axis and includes a liquid permeable inner surface for facing the wearer, an outer surface for facing away from the wearer, an absorbent body disposed therebetween, and a front waist region, a back waist region, and a crotch region extending longitudinally between and interconnecting the front and back waist regions. The article also includes a front side panel attached to the front waist region and a back side panel attached to the back waist region, wherein each side panel has an attachment edge and a free edge, the front and back side panels being one of permanently attached and releasably fastenable to define a wear configuration of the absorbent article having a waist opening and a leg opening spaced from the waist opening, wherein the front and back side panels each extend from the waist opening to the leg opening. The article also includes a rigid finger tab attached to and extending from the free edge of one of the front and back side panels, the finger tab having a finger tab stiffness and the side panel having a side panel stiffness, wherein the finger tab stiffness is at least two times greater than the side panel stiffness of the side panel to which the finger tab is fastened.

Other features of the disclosure will be in part apparent and in part pointed out hereinafter. Other objects and advantages of the present disclosure will become more apparent to those skilled in the art in view of the following description and the accompanying drawings.

BRIEF DESCRIPTION OF THE DRAWINGS

The present disclosure will be more fully understood, and further features will become apparent, when reference is made to the following detailed description and the accompanying drawings. The drawings are merely representative and are not intended to limit the scope of the claims.

Figure 1:
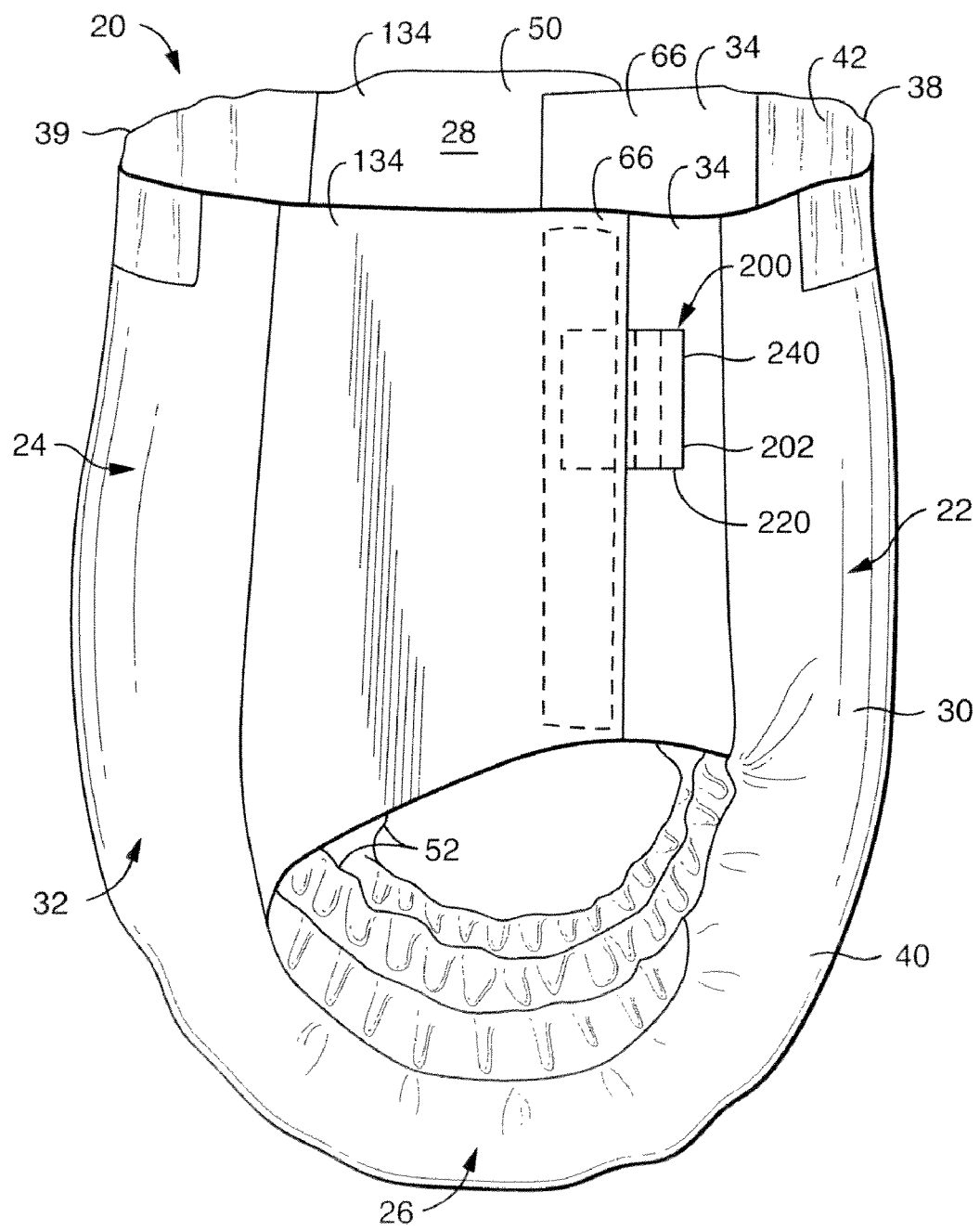
FIG. 1 is a side perspective view of one aspect of a personal wear article in the form of a pair of training pants having a finger tab system illustrated in a fastened condition thereof.

Repeat use of reference characters in the present specification and drawings is intended to represent the same or analogous features or elements of the present disclosure. The drawings are representational and are not necessarily drawn to scale. Certain proportions thereof might be exaggerated, while others might be minimized.

DETAILED DESCRIPTION

It is to be understood by one of ordinary skill in the art that the present discussion is a description of exemplary aspects of the present disclosure only, and is not intended as limiting the broader aspects of the present disclosure.

Within the context of this specification, each term or phrase below will include the following meaning or meanings.

"Bonded" refers to the joining, adhering, connecting, attaching, or the like, of two elements. Two elements will be considered to be bonded together when they are bonded directly to one another or indirectly to one another, such as when each is directly bonded to intermediate elements.

"Connected" refers to the joining, adhering, bonding, attaching, or the like, of two elements. Two elements will be considered to be connected together when they are connected directly to one another or indirectly to one another, such as when each is directly connected to intermediate elements.

"Cross direction" refers to the width of a fabric in a direction generally perpendicular to the direction in which it is produced, as opposed to "machine direction" that refers to the length of a fabric in the direction in which it is produced.

Figure 3:
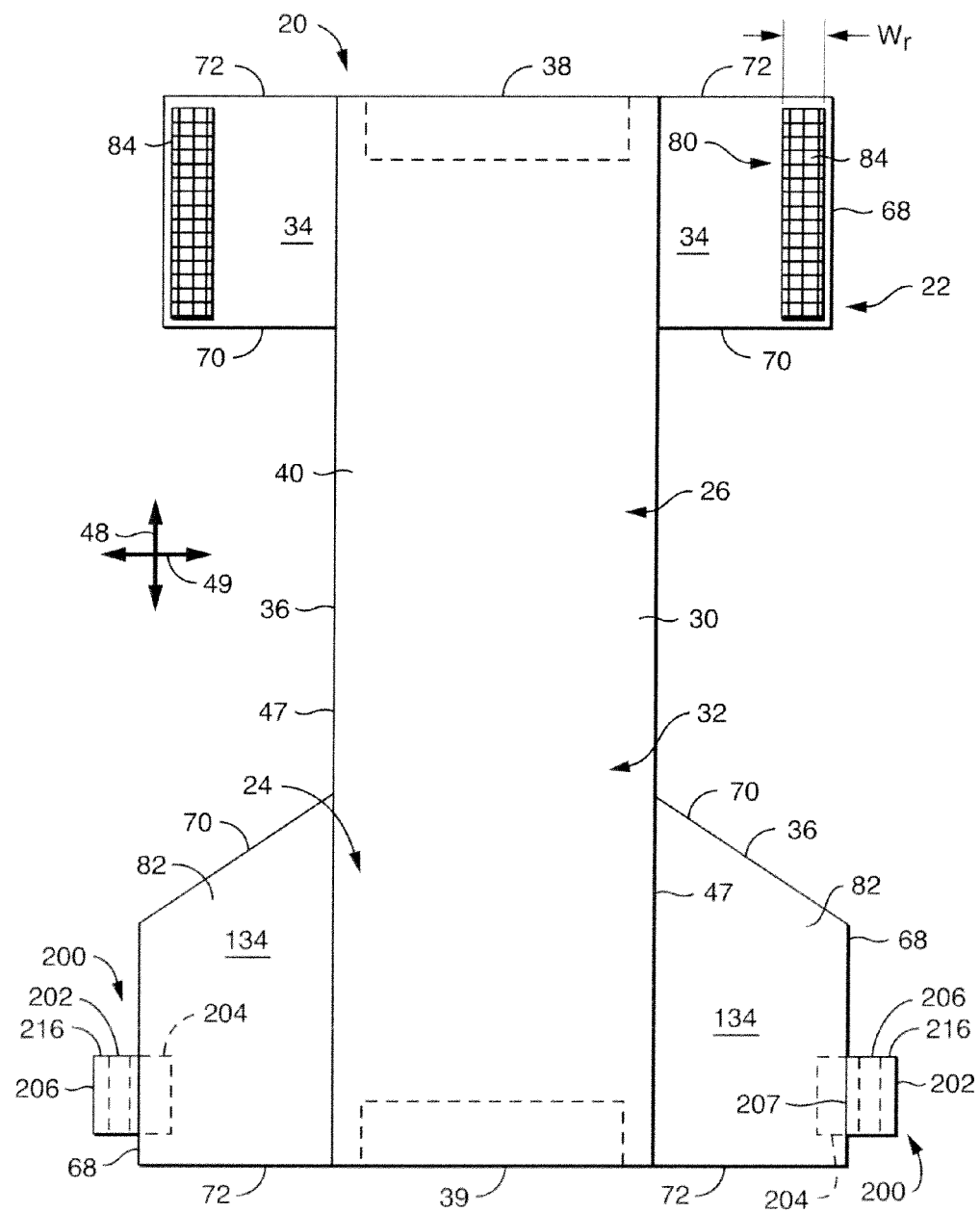
FIG. 3 is a bottom plan view of the training pants of FIG. 1 in an unfastened, unfolded and laid flat condition, and showing the surface of the training pants that faces away from the wearer.

"Cross direction assembly" refers to a process in which disposable absorbent products are manufactured in an orientation in which the products are connected side-to-side, in the transverse direction shown by arrow 49 in FIG. 3, a process utilizing a cross direction assembly entails products traveling through a converting machine parallel to the direction of arrow 49, as opposed to "machine direction assembly" in which the products are connected end-to-end or waist-to-waist.

"Disposable" refers to articles that are designed to be discarded after a limited use rather than being laundered or otherwise restored for reuse.

"Disposed," "disposed on," and variations thereof are intended to mean that one element can be integral with another element, or that one element can be a separate structure bonded to or placed with or placed near another element.

"Elastic," "elasticized" and "elasticity" mean that property of a material or composite by virtue of which it tends to recover its original size and shape after removal of a force causing a deformation.

"Elastomeric" refers to a material or composite that can be elongated by at least 25 percent of its relaxed length and that will recover, upon release of the applied force, at least 10 percent of its elongation. It is generally preferred that the elastomeric material or composite be capable of being elongated by at least 100 percent, more preferably by at least 300 percent, of its relaxed length and recover, upon release of an applied force, at least 50 percent of its elongation.

"Fabrics" is used to refer to all of the woven, knitted and nonwoven fibrous webs.

"Film" refers to a thermoplastic film made using a film extrusion and/or foaming process, such as a cast film or blown film extrusion process. The term includes apertured films, slit films, and other porous films that constitute liquid transfer films, as well as films that do not transfer liquid.

"Flexible" refers to materials that are compliant and that will readily conform to the general shape and contours of the wearer's body.

"Hydrophilic" describes fibers or the surfaces of fibers that are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System, or a substantially equivalent system. When measured with this system, fibers having contact angles less than 90 are designated "wettable" or hydrophilic, while fibers having contact angles greater than 90 are designated "nonwettable" or hydrophobic.

"Integral" or "integrally" is used to refer to various portions of a single unitary element rather than separate structures bonded to or placed with or placed near one another.

"Layer" when used in the singular can have the dual meaning of a single element or a plurality of elements.

"Liquid impermeable," when used in describing a layer or multi-layer laminate, means that a liquid, such as urine, will not pass through the layer or laminate, under ordinary use conditions, in a direction generally perpendicular to the plane of the layer or laminate at the point of liquid contact. Liquid, or urine, can spread or be transported parallel to the plane of the liquid impermeable layer or laminate, but this is not considered to be within the meaning of "liquid impermeable" when used herein.

"Liquid permeable material" or "liquid water-permeable material" refers to a material present in one or more layers, such as a film, nonwoven fabric, or open-celled foam, which is porous, and which is water permeable due to the flow of water and other aqueous liquids through the pores. The pores in the film or foam, or spaces between fibers or filaments in a nonwoven web, are large enough and frequent enough to permit leakage and flow of liquid water through the material.

Figure 2:
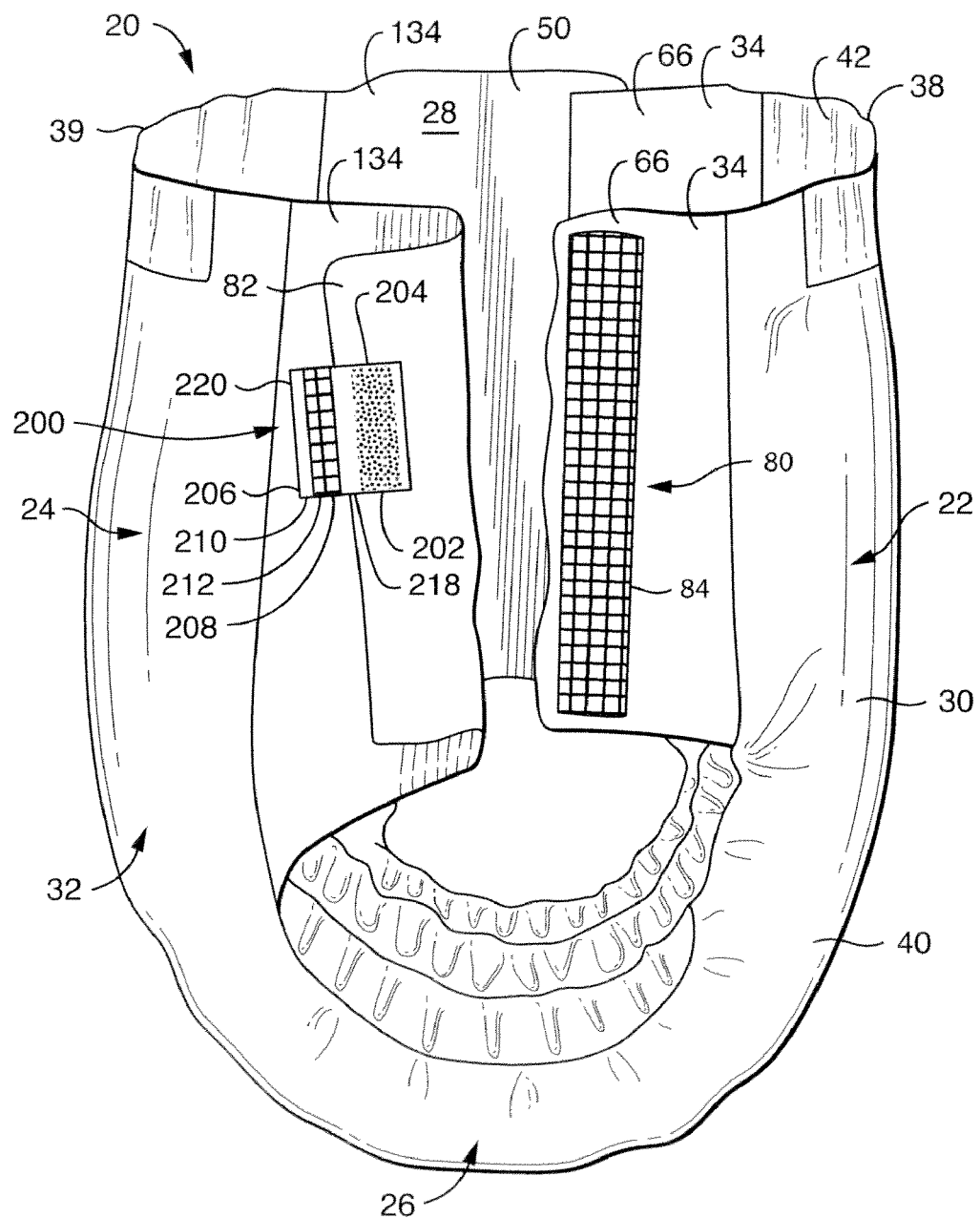
FIG. 2 is a side perspective similar to FIG. 1 with a primary or article fastening system of the training pants in a unfastened condition on one side of the training pants and the finger tab system also in an unfastened condition.

"Longitudinal" and "transverse" have their customary meaning, as indicated by the longitudinal and transverse axes depicted in FIGS. 2 and 3. The longitudinal axis lies in the plane of the article and is generally parallel to a vertical plane that bisects a standing wearer into left and right body halves when the article is worn. The transverse axis lies in the plane of the article generally perpendicular to the longitudinal axis. The article as illustrated is longer in the longitudinal direction than in the transverse direction.

"Machine direction" refers to the length of a fabric in the direction in which it is produced, as opposed to "cross direction" that refers to the width of a fabric in a direction generally perpendicular to the machine direction.

"Machine direction assembly" refers to a process in which disposable absorbent products are manufactured in an orientation in which the products are connected end-to-end or waist-to-waist, in the longitudinal direction shown by arrow 48 in FIGS. 2 and 3, a process utilizing a machine direction assembly entails products traveling through a converting machine parallel to the direction of arrow 48, as opposed to "cross direction assembly" in which the products are connected side-to-side.

"Meltblown fiber" means fibers formed by extruding a molten thermoplastic material through a plurality of fine, usually circular, die capillaries as molten threads or filaments into converging high velocity heated gas (e.g., air) streams that attenuate the filaments of molten thermoplastic material to reduce their diameter, which can be to microfiber diameter. Thereafter, the meltblown fibers are carried by the high velocity gas stream and are deposited on a collecting surface to form a web of randomly dispersed meltblown fibers. Such a process is disclosed for example, in U.S. Pat. No. 3,849,241 to Butin et al. Meltblown fibers are microfibers that can be continuous or discontinuous, are generally smaller than about 0.6 denier, and are generally self bonding when deposited onto a collecting surface. Meltblown fibers used in the present disclosure are preferably substantially continuous in length.

"Member" when used in the singular can have the dual meaning of a single element or a plurality of elements.

"Nonwoven" and "nonwoven web" refer to materials and webs of material that are formed without the aid of a textile weaving or knitting process.

"Operatively joined," in reference to the attachment of an elastic member to another element, means that the elastic member when attached to or connected to the element, or treated with heat or chemicals, by stretching, or the like, gives the element elastic properties; and with reference to the attachment of a non-elastic member to another element, means that the member and element can be attached in any suitable manner that permits or allows them to perform the intended or described function of the joinder. The joining, attaching, connecting or the like can be either directly, such as joining either member directly to an element, or can be indirectly by means of another member disposed between the first member and the first element.

"Peel force" and "peel strain" refer to forces that tend to pull two adjoining bodies away from one another in opposite directions generally perpendicular to a plane in which the bodies are joined.

"Permanently bonded" refers to the joining, adhering, connecting, attaching, or the like, of two elements of an absorbent garment such that the elements tend to be and remain bonded during normal use conditions of the absorbent garment.

"Polymers" include, but are not limited to, homopolymers, copolymers, such as for example, block, graft, random and alternating copolymers, terpolymers, etc. and blends and modifications thereof. Furthermore, unless otherwise specifically limited, the term "polymer" shall include all possible geometrical configurations of the material. These configurations include, but are not limited to isotactic, syndiotactic and atactic symmetries.

"Refastenable" refers to the property of two elements being capable of releasable attachment, separation, and subsequent releasable reattachment without substantial permanent deformation or rupture.

"Releasably attached," "releasably engaged" and variations thereof refer to two elements being connected or connectable such that the elements tend to remain connected absent a separation force applied to one or both of the elements, and the elements being capable of separation without substantial permanent deformation or rupture. The required separation force is typically beyond that encountered while wearing the absorbent garment.

"Shearing strain" refers to forces that tend to produce an opposite but parallel sliding motion between two bodies' planes.

"Spunbonded fiber" refers to small diameter fibers that are formed by extruding molten thermoplastic material as filaments from a plurality of fine capillaries of a spinnerette having a circular or other configuration, with the diameter of the extruded filaments then being rapidly reduced as by, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, U.S. Pat. No. 3,502,538 to Petersen, and U.S. Pat. No. 3,542,615 to Dobo et al., each of which is incorporated herein in its entirety by reference. Spunbond fibers are quenched and generally not tacky when they are deposited onto a collecting surface. Spunbond fibers are generally continuous and often have average deniers larger than about 0.3, more particularly, between about 0.6 and 10.

"Stretchable" means that a material can be stretched, without breaking, to at least 150% of its initial (unstretched) length in at least one direction, suitably to at least 200% of its initial length, desirably to at least 250% of its initial length.

"Superabsorbent" or "superabsorbent material" refers to a water-swellable, water-insoluble organic or inorganic material capable, under the most favorable conditions, of absorbing at least about 15 times its weight and, more desirably, at least about 30 times its weight in an aqueous solution containing 0.9 weight percent sodium chloride. The superabsorbent materials can be natural, synthetic and modified natural polymers and materials. In addition, the superabsorbent materials can be inorganic materials, such as silica gels, or organic compounds such as cross-linked polymers.

"Surface" includes any layer, film, woven, nonwoven, laminate, composite, or the like, whether pervious or impervious to air, gas, and/or liquids.

"Thermoplastic" describes a material that softens when exposed to heat and that substantially returns to a nonsoftened condition when cooled to room temperature.

These terms can be defined with additional language in the remaining portions of the specification.

Referring now to the drawings and in particular to FIG. 1, a personal wear absorbent article according to one aspect is illustrated in the form of a pants-type article for wear about a wearer's waist, and more particularly in the form of children's toilet training pants, indicated in its entirety by the reference numeral 20. The term absorbent generally refers to articles that can be placed against or in proximity to the body of the wearer to absorb and/or retain various liquid wastes discharged from the body. The absorbent article can be disposable, which refers to articles that are intended to be discarded after a limited period of use instead of being laundered or otherwise restored for reuse. It is understood that the concepts described herein are suitable for use with various other pants-type articles such as adult incontinence articles, as well as other articles intended for personal wear such as clothing, diapers, feminine hygiene products, medical garments, surgical pads and bandages, other personal care or health care garments, and the like without departing from the scope of the present disclosure.

By way of illustration only, various materials and methods for constructing the training pants 20 are disclosed in PCT Patent Application WO 00/37009 published Jun. 29, 2000 by A. Fletcher et al; U.S. Pat. No. 4,940,464 issued Jul. 10, 1990 to Van Gompel et al.; and U.S. Pat. No. 5,766,389 issued Jun. 16, 1998 to Brandon et al., which are incorporated herein by reference.

The present disclosure is directed to a process for making a pant-like absorbent garment having refastenable fasteners, such as hook and loop fasteners, on the side panels for ease of removal and donning of the absorbent garment without complete removal of a wearer's clothing. A pant design advantageous for either an end-to-end or side-by-side manufacturing process increases the ease of opening a mechanical fastener side seam by enabling the user to manipulate a finger tab in a less resistant longitudinal peel motion as compared to a more resistant transverse peel motion. Training pant mechanical fasteners typically have a longitudinal disengagement peel strength that is significantly less than the transverse disengagement peel strength. The transverse disengagement is done over a shorter distance, but its greater width requires a greater disengagement force per unit (e.g., mm) of peel. Conversely, the longitudinal disengagement is done over a greater distance, but its lesser width requires a lesser disengagement force per unit (e.g., mm) of peel.

The pair of training pants 20 is illustrated in FIG. 1 in a fully pre-assembled (i.e., as assembled during initial manufacture) configuration (broadly referred to herein as a wear configuration of the pants, i.e., absorbent article) and in FIG. 2 in a partially unfastened condition. The training pants 20 includes a front waist region 22, a back waist region 24, a crotch region 26 extending longitudinally between and interconnecting the front and back waist regions along a longitudinal direction of the pants, an inner surface 28 configured for contiguous relationship with the wearer, and an outer surface 30 opposite the inner surface. With additional reference to FIGS. 3 and 4, the training pants 20 also has a pair of laterally opposite side edges 36 and a pair of longitudinally opposite waist edges, respectively designated front waist edge 38 and back waist edge 39. The front waist region 22 is contiguous with the front waist edge 38, and the back waist region 24 is contiguous with the back waist edge 39.

Figure 4:
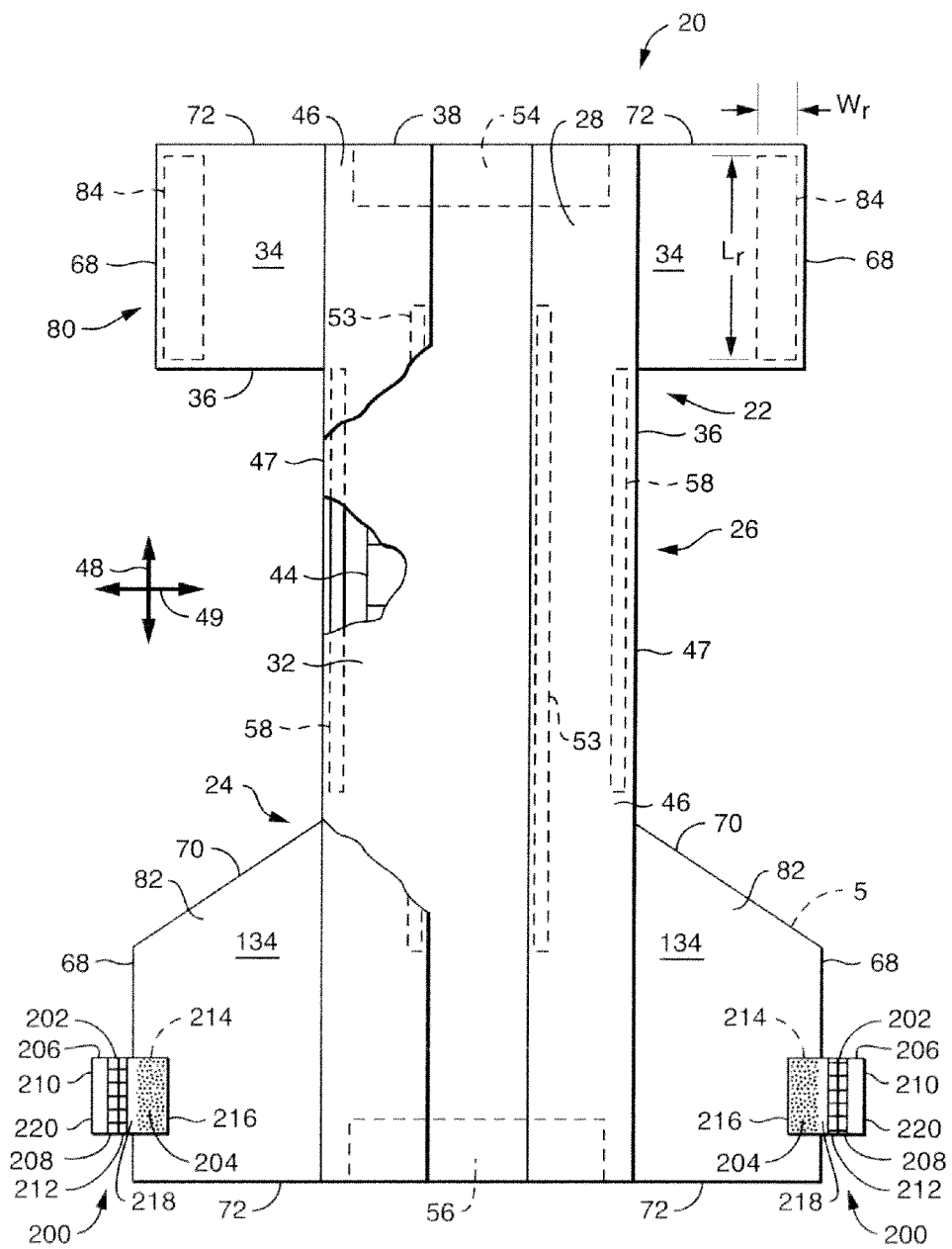
FIG. 4 is a top plan view similar to FIG. 3 showing the surface of the training pants that faces the wearer when worn and with portions cut away to show underlying features.

The illustrated pants 20 includes a central absorbent assembly, generally indicated at 32, which when laid flat as in FIGS. 3 and 4 can be rectangular or any other desired shape. A pair of laterally opposite front side panels 34 extends outward from the absorbent assembly 32 at the front waist region 22 (thereby forming transversely outer portions of the front waist region, and more broadly in part forming transversely opposite sides of the training pants). Laterally opposite back side panels 134 extend outward from the absorbent assembly 32 at the back waist region 24 (thereby forming transversely outer portions of the back waist region, and together with the front side panels 34 further defining the sides of the pants).

The central absorbent assembly 32 of the illustrated aspect includes an outer cover 40 and a bodyside liner 42 (FIGS. 1 and 2) connected to the outer cover in a superposed relation by suitable means such as adhesives, ultrasonic bonds, thermal bonds or other conventional techniques. An absorbent structure 44 (FIG. 4) is disposed between the outer cover and the bodyside liner. A pair of containment flaps 46 (FIG. 4) is secured to the bodyside liner 42 for inhibiting the lateral flow of body exudates. The central absorbent assembly 32 has opposite ends that form portions of the front and back waist edges 38 and 39, and opposite side edges 47 that form portions of the side edges 36 of the training pants 20 (FIGS. 3 and 4).

The absorbent assembly 32 and side panels 34, 134 can include two or more separate elements, as shown in FIGS. 1 and 2, or they can be integrally formed. Integrally formed side panels 34, 134 and absorbent assembly 32 would include at least some common materials, such as the bodyside liner, flap composite, outer cover, other materials and/or combinations thereof, and could define a one-piece elastic, stretchable, or nonstretchable pants 20. For further reference, arrows 48 and 49 in FIGS. 3 and 4 depict the orientation of a longitudinal axis and a transverse or lateral axis, respectively, of the training pants 20.

With the training pants 20 in the fastened condition as illustrated fully in FIG. 1 and partially in FIG. 2, the front and back side panels 34, 134 are fastened to each other by a primary, or article fastening system 80 to define the pre-assembled three-dimensional wear configuration of the pants, having a waist opening 50 and a pair of leg openings 52. The front waist region 22 includes the portion of the training pants 20 that, when worn, is positioned at least in part on the front of the wearer while the back waist region 24 includes the portion of the training pants that is positioned at least in part on the back of the wearer. The crotch region 26 of the training pants 20 includes the portion of the training pants 20 that is positioned between the legs of the wearer and covers the lower torso of the wearer.

The front and back side panels 34 and 134 include the portions of the training pants 20 (and more particularly of the front and back waist regions 22, 24) that, when worn, are positioned on the hips of the wearer. The attached side panels 34, 134 thus broadly define the transversely opposite sides of the pants 20 at an engagement seam 66 along which the fastening system 80 releasably attaches the front and back side panels. The waist edges 38 and 39 of the training pants 20 are configured to encircle the waist of the wearer and together define the waist opening 50 (FIG. 1). Portions of the side edges 36 in the crotch region 26 generally define the leg openings 52.

The central absorbent assembly 32 is configured to contain and/or absorb exudates discharged from the wearer. For example, the containment flaps 46 are configured to provide a barrier to the transverse flow of body exudates. A flap elastic member 53 (FIG. 4) can be operatively joined with each containment flap 46 in any suitable manner as is well known in the art. The elasticized containment flaps 46 define a partially unattached edge that assumes an upright configuration in at least the crotch region 26 of the training pants 20 to form a seal against the wearer's body. The containment flaps 46 can be located along the side edges 36 of the pants 20, and can extend longitudinally along the entire length of the absorbent assembly 32 or can only extend partially along the length of the absorbent assembly. Suitable constructions and arrangements for the containment flaps 46 are generally well known to those skilled in the art and are described in U.S. Pat. No. 4,704,116 issued Nov. 3, 1987 to Enloe, which is incorporated herein by reference.

To further enhance containment and/or absorption of body exudates, the training pants 20 also suitably includes a front waist elastic member 54 (FIG. 4), a rear waist elastic member 56, and leg elastic members 58, as are known to those skilled in the art. The waist elastic members 54 and 56 can be attached to the outer cover 40 and/or the bodyside liner 42 along the opposite waist edges 38 and 39, and can extend over part or all of the waist edges. The leg elastic members 58 can be attached to the outer cover 40 and/or the bodyside liner 42 along the opposite side edges 36 and positioned in the crotch region 26 of the training pants 20. The leg elastic members 58 can be longitudinally aligned along each side edge 47 of the absorbent assembly 32.

The flap elastic members 53, the waist elastic members 54 and 56, and the leg elastic members 58 can be formed of any suitable elastic material. As is well known to those skilled in the art, suitable elastic materials include sheets, strands or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example with the application of heat, such that elastic retractive forces are imparted to the substrate. In one particular aspect, for example, the leg elastic members 58 include a plurality of dry-spun coalesced multifilament spandex elastomeric threads sold under the trade name LYCRA® and available from E.I. Du Pont de Nemours and Company, Wilmington, Del., U.S.A.

The outer cover 40 suitably includes a material that is substantially liquid impermeable. The outer cover 40 can be a single layer of liquid impermeable material, but more suitably includes a multi-layered laminate structure in which at least one of the layers is liquid impermeable. For instance, the outer cover 40 can include a liquid permeable outer layer and a liquid impermeable inner layer that are suitably joined together by a laminate adhesive, ultrasonic bonds, thermal bonds, or the like. Suitable laminate adhesives can be applied continuously or intermittently as beads, a spray, parallel swirls, or the like. The liquid permeable outer layer can be any suitable material and is desirably one that provides a generally cloth-like texture. The outer layer can also be made of those materials of which the liquid permeable bodyside liner 42 is made. While it is not a necessity for the outer layer to be liquid permeable, it is suitable that it provides a relatively cloth-like texture to the wearer.

The inner layer of the outer cover 40 can be both liquid and vapor impermeable, or it can be liquid impermeable and vapor permeable. The inner layer can be manufactured from a thin plastic film, although other flexible liquid impermeable materials can also be used. The inner layer, or the liquid impermeable outer cover 40 when a single layer, prevents waste material from wetting articles, such as bed sheets and clothing, as well as the wearer and caregiver.

If the outer cover 40 is a single layer of material, it can be embossed and/or matte finished to provide a more cloth-like appearance. As earlier mentioned, the liquid impermeable material can permit water vapors to escape from the interior of the disposable absorbent article, while still preventing liquids from passing through the outer cover 40. One suitable "breathable" material is composed of a microporous polymer film or a nonwoven fabric that has been coated or otherwise treated to impart a desired level of liquid impermeability.

It is also contemplated that the outer cover 40 can be stretchable, and more suitably elastic. In particular, the outer cover 40 is suitably stretchable and more suitably elastic in at least the transverse or circumferential direction of the pants 20. In other aspects the outer cover can be stretchable, and more suitably elastic, in both the transverse and the longitudinal direction.

The liquid permeable bodyside liner 42 is illustrated as overlying the outer cover 40 and absorbent core 44, and can, but need not, have the same dimensions as the outer cover 40. The bodyside liner 42 is suitably compliant, soft feeling, and non-irritating to the child's skin. Further, the bodyside liner 42 can be less hydrophilic than the absorbent structure 44 to present a relatively dry surface to the wearer and permit liquid to readily penetrate through its thickness. Alternatively, the bodyside liner 42 can be more hydrophilic or can have essentially the same affinity for moisture as the absorbent structure 44 to present a relatively wet surface to the wearer to increase the sensation of being wet. This wet sensation can be useful as a training aid. The hydrophilic/hydrophobic properties can be varied across the length, width and/or depth of the bodyside liner 42 and absorbent structure 44 to achieve the desired wetness sensation or leakage performance.

The bodyside liner 42 can be manufactured from a wide selection of web materials, such as synthetic fibers (for example, polyester or polypropylene fibers), natural fibers (for example, wood or cotton fibers), a combination of natural and synthetic fibers, porous foams, reticulated foams, apertured plastic films, or the like. Various woven and nonwoven fabrics can be used for the bodyside liner 42.

For example, the bodyside liner can be composed of a meltblown or spunbonded web of polyolefin fibers. The bodyside liner can also be a bonded-carded web composed of natural and/or synthetic fibers. The bodyside liner can be composed of a substantially hydrophobic material, and the hydrophobic material can, optionally, be treated with a surfactant or otherwise processed to impart a desired level of wettability and hydrophilicity. The surfactant can be applied by any conventional means, such as spraying, printing, brush coating or the like. The surfactant can be applied to the entire bodyside liner 42 or can be selectively applied to particular sections of the bodyside liner, such as the medial section along the longitudinal center line.

The bodyside liner 42 can also be stretchable, and more suitably elastic. In particular, the bodyside liner 42 is suitably stretchable and more suitably elastic in at least the transverse 49, or circumferential direction of the pants 20. In other aspects, the bodyside liner 42 can be stretchable, and more suitably elastic, in both the transverse 49 and the longitudinal 48 directions.

As noted previously, the illustrated training pants 20 have front and back side panels 34 and 134 defining transversely opposite sides of the pants in the wear configuration of the pants. The side panels 34, 134 can be permanently attached along seams 66 to the central absorbent assembly 32 in the respective front and back waist regions 22 and 24. More particularly, as seen best in FIGS. 2 and 3, the front side panels 34 can be permanently attached to and extend transversely outward beyond the side edges 47 of the absorbent assembly 32 in the front waist region 22, and the back side panels 134 can be permanently attached to and extend transversely outward beyond the side edges of the absorbent assembly in the back waist region 24. The side panels 34 and 134 can be attached to the absorbent assembly 32 using attachment means known to those skilled in the art such as adhesive, thermal, pressure or ultrasonic bonding. Alternatively, the side panels 34 and 134 can be formed as an integral portion of a component of the absorbent assembly 32. For example, the side panels can include a generally wider portion of the outer cover 40, the bodyside liner 42, and/or another component of the absorbent assembly 32.

The front and back side panels 34, 134 each have an outer edge 68 spaced laterally from the seam 66, a leg end edge 70 disposed toward the longitudinal center of the training pants 20, and a waist end edge 72 disposed toward a longitudinal end of the training pants. The leg end edge 70 and waist end edge 72 extend from the side edges 47 of the absorbent assembly 32 to the outer edges 68. The front and back side panels 34, 134 also include a free edge that is the unattached edge of the side panel including the leg end edge 70, the outer edge 68, and the waist end edge 72. The leg end edges 70 of the side panels 34 and 134 form part of the side edges 36 of the training pants 20. The leg end edges 70 of the illustrated aspect are suitably curved and/or angled relative to the transverse axis 49 to provide a better fit around the wearer's legs. However, it is understood that only one of the leg end edges 70 can be curved or angled, such as the leg end edge of the back waist region 24, or neither of the leg end edges can be curved or angled, without departing from the scope of this disclosure. The waist end edges 72 are suitably parallel to the transverse axis 49. The waist end edges 72 of the front side panels 34 form part of the front waist edge 38 of the training pants 20, and the waist end edges 72 of the back side panels 134 form part of the back waist edge 39 of the pants.

The side panels 34, 134 suitably, although not necessarily, include a stretchable material capable of stretching in a direction generally parallel to the transverse axis 49 of the training pants 20. More suitably the side panels 34, 134 include an elastic material. Suitable elastic materials, as well as one process of incorporating stretchable side panels into training pants, are described in the following U.S. Pat. No. 4,940,464 issued Jul. 10, 1990 to Van Gompel et al.; U.S. Pat. No. 5,224,405 issued Jul. 6, 1993 to Pohjola; U.S. Pat. No. 5,104,116 issued Apr. 14, 1992 to Pohjola; and U.S. Pat. No. 5,046,272 issued Sep. 10, 1991 to Vogt et al.; all of which are incorporated herein by reference. In particular aspects, the stretch material can include a stretch-thermal laminate (STL), a neck-bonded laminate (NBL), a reversibly necked laminate, or a stretch-bonded laminate (SBL) material. Methods of making such materials are well known to those skilled in the art and described in U.S. Pat. No. 4,663,220 issued May 5, 1987 to Wisneski et al.; U.S. Pat. No. 5,226,992 issued Jul. 13, 1993 to Morman; European Patent Application No. EP 0 217 032 published on Apr. 8, 1987 in the name of Taylor et al.; and PCT application WO 01/88245 in the name of Welch et al.; all of which are incorporated herein by reference. Other suitable materials are described in U.S. patent application Ser. Nos. 12/649,508 to Welch et al. and 12/023,447 to Lake et al., all of which are incorporated herein by reference.

In one particularly suitable aspect, at least the front side panels 34 and more suitably both the front and back side panels 34, 134 include a vertical filament laminate (VFL) material. A VFL is a composite material having at least one gatherable layer such as a non-woven material and at least one elastic layer. The layers are joined together when the elastic layer is extended from its original condition so that upon relaxing the layers, the gatherable layer is gathered. The composite can be stretched to the extent that the non-elastic material gathered between the bond locations allows the elastic material to elongate. One type of vertical filament laminate is disclosed, for example, by U.S. Pat. No. 6,916,750 to Thomas et al., the content of which is incorporated herein by reference to the extent it does not conflict herewith. More suitably, the front and back side panels include a VFL in which two non-woven (gatherable) layers sandwich an elastic layer so that both faces of the VFL are gatherable. The rugosities formed in the gatherable layers of such a VFL material allow the VFL material to be used as a loop component of a fastening system.

Alternatively, the side panel material can include other woven or nonwoven materials, such as those described above as being suitable for the outer cover 40 or bodyside liner 42; mechanically pre-strained composites; or stretchable but inelastic materials.

The absorbent structure 44 can be any structure that is generally compressible, conformable, non-irritating to the wearer's skin and capable of absorbing and retaining liquid body exudates, and can be manufactured in a wide variety of sizes and shapes, and from a wide variety of absorbent materials commonly used in the art. For example, the absorbent structure 44 suitably includes a matrix of absorbent fibers, and more particularly hydrophilic fibers, such as a web of cellulosic fluff. In a particularly suitable aspect, the absorbent structure 44 includes a matrix of cellulosic fluff, such as wood pulp fluff, and superabsorbent particles. The wood pulp fluff can be exchanged with synthetic, polymeric, meltblown fibers or short cut homofil bicomponent synthetic fibers and natural fibers. The superabsorbent particles can be substantially homogeneously mixed with the hydrophilic fibers or can be nonuniformly mixed. The fluff and superabsorbent particles can also be selectively placed into desired zones of the absorbent structure 44 to better contain and absorb body exudates. The concentration of the superabsorbent particles can also vary through the thickness of the absorbent core 44. Alternatively, the absorbent structure 44 can include a laminate of fibrous webs and superabsorbent material or other suitable means of maintaining a superabsorbent material in a localized area.

Suitable superabsorbent materials can be selected from natural, synthetic, and modified natural polymers and materials. The superabsorbent materials can be inorganic materials, such as silica gels, or organic compounds, such as crosslinked polymers, for example, sodium neutralized polyacrylic acid. Suitable superabsorbent materials are available from various commercial vendors, such as Dow Chemical Company located in Midland, Mich., U.S.A., and Stockhausen GmbH & Co. KG, D-47805 Krefeld, Federal Republic of Germany.

In one aspect, the absorbent structure 44 includes a blend of wood pulp fluff and superabsorbent material. As a general rule, the superabsorbent material is present in the absorbent structure 44 in an amount of from 0 to about 90 weight percent based on total weight of the absorbent assembly. The absorbent structure 44 suitably has a density within the range of about 0.10 to about 0.35 grams per cubic centimeter. The absorbent structure 44 can be wrapped or encompassed by a suitable wrap that can help maintain the integrity and/or shape of the absorbent assembly.

The article fastening system 80 includes laterally opposite first article fastening components 82 adapted for refastenable engagement to corresponding second article fastening components 84. In one aspect, a front or outer surface of each of the article fastening components 82, 84 includes a plurality of engaging elements. The engaging elements of the first article fastening components 82 are adapted to repeatedly engage and disengage corresponding engaging elements of the second article fastening components 84 to releasably secure the pants 20 in its three-dimensional configuration. The article fastening system 80 provides an attachment of a strength sufficient to maintain the article in a wear configuration during use of the pants 20 by the wearer.

The article fastening components 82, 84 can include any refastenable fasteners suitable for absorbent articles, such as adhesive fasteners, cohesive fasteners, mechanical fasteners, or the like. In particular aspects, the article fastening components 82, 84 include mechanical fastening components for improved performance. Suitable mechanical fastening components can be provided by interlocking geometric shaped materials, such as hooks, loops, bulbs, mushrooms, arrowheads, balls on stems, male and female mating components, buckles, snaps, or the like.

In the illustrated aspect, the first article fastening components 82 (i.e., one on each side of the training pants 20) include loop fasteners and the second article fastening components 84 include complementary hook fasteners. Alternatively, the first article fastening components 82 can include hook fasteners and the second article fastening components 84 can include complementary loop fasteners. In another aspect, the article fastening components 82, 84 can include interlocking similar surface fasteners, or adhesive and cohesive fastening elements such as an adhesive fastener and an adhesive-receptive landing zone or material; or the like. Although the training pants 20 illustrated in FIG. 1 show the back side panels 134 overlapping the front side panels 34 upon connection thereto, which is convenient, the training pants 20 can also be configured so that the front side panels overlap the back side panels when connected. One skilled in the art will recognize that the shape, density and polymer composition of the hooks and loops can be selected to obtain the desired level of engagement between the article fastening components 82, 84. A more aggressive hook material can include a material with a greater average hook height and/or a greater percentage of directionally-aligned hooks. When engaged, the article fastening components 82, 84 of the illustrated aspect define the refastenable engagement seams 66 (FIG. 2).

As discussed above, in one particularly suitable aspect, as best seen in FIGS. 2 and 4, the back side panels 134 are constructed so that the inner surfaces of the respective back side panels define loop article fastening components 82 (i.e., the back side panels 134 and the article fastening components 82 are formed integrally). It is understood, however, that the loop article fastening components 82 can be formed separate from the back side panels 134 and attached thereto, such as by adhesive, thermal bonds, ultrasonic bonds, pressure bonds or other suitable techniques without departing from the scope of this disclosure.

An easy opening side (EOS) finger tab is attached to and overhangs the cross-direction side panel edge for ease of opening. This easy opening side design causes the user to grab and pull the EOS tab in a machine-direction, longitudinal peel motion. A typical side seam attachment/engagement zone has a longitudinal length four times greater than its transverse width. As a result, a longitudinal motion peel motion requires at least four times less energy to open the side seam as compared to a transverse or cross-direction peel motion. A cut-in-place type of operation well known in the business can place the EOS tab at the panel edge such that the EOS tab feature extends from the pant edge. This enables the user to grab and pull in a longitudinal motion.

With particular reference to FIGS. 1 and 2, a secondary, or finger tab system, generally indicated at 200, is provided for use in opening the side seam 66 of the training pants 20. In one aspect illustrated in FIGS. 2 and 4, the finger tab system includes a tab 202 attached to each of the back side panels 134 (broadly, to the transversely opposite sides of the training pants 20) and extending in part transversely outward of the respective back side panels 134 for opposed relationship with the corresponding front side panels 34 in the wear configuration of the pants 20. FIGS. 1-4 illustrate the general arrangement of a finger tab 202 of the present disclosure; the details of various aspects of finger tabs 202 are illustrated in FIGS. 5-8.

The finger tab 202 includes first and second ends 205, 203 and a distal point 209, the first end 205 of the finger tab 202 being attached to one of the front or back side panels 34, 134 adjacent the outer edge 68 of that front or back side panel 34, 134. The distal point 209 is the point on the finger tab 202 that is furthest from the outer edge 68 in a transverse direction. In some aspects, the distal point 209 can be a point or a line. The finger tab 202 also includes a tab line 207 where the finger tab 202 intersects the outer edge 68 of one of the front and back side panels 34, 134. The finger tab system 200 includes an aperture 211 disposed between the distal point 209 of the finger tab 202 and the tab line 207.

As seen best in FIG. 2, each finger tab 202 includes an attachment region 204 at a proximal end of the tab 202 and at which the finger tab 202 is attached to the respective back side panel 134, and a tab region 206 at the distal end of the tab 202 extending transversely outward from the attachment region 204. More suitably, the tab region 206 of the finger tab 202 can include at least one tab fastener region 208 having a tab fastening component 212 for use in securing the finger tab 202 to the training pants 20, and can further include a grip region 210 transversely outward of the tab fastener region 208 for use in manually gripping and manipulating the finger tab 202 relative to the pants 20. The finger tab 202 forms a tab line 207 where the finger tab 202 intersects the front or back side panel 34, 134.

The tab region 206 via its fastener region 208 can be releasably fastened to a side panel when the pants 20 is in a wear configuration. Such a releasable attachment by the tab region 206 alone, however, provides an attachment strength that is insufficient to maintain the pants 20 in a wear configuration during use of the pants 20 by the wearer.

The tab fastening component 212, if present, of the illustrated tab fastener region 208 includes a hook fastener. The outer surface of each front side panel 34 suitably defines a corresponding fastening component, e.g., a loop fastener, to permit the finger tab 202 on each side of the pants 20 to be fastened at its tab fastener region 208 to the respective front side panel (i.e., broadly, to the pants 20) in the wear configuration of the pants 20. For example, the front side panel 34 in one particularly suitable aspect can be constructed of VFL material as described previously so that the outer surface of the front side panel 34 itself defines a loop fastening component. Alternatively, a loop fastener component (not shown) can be formed separately from the front side panel 34 and attached to the panel outer surface without departing from the scope of this disclosure. The outer facing surface 30 of the outer cover 40 of the pants 20 is also suitably constructed to define a loop fastener, such as by forming the outer cover of a material that defines a loop fastening component (e.g., VFL or other suitable material) or by forming a separate loop fastening component and attaching it to the outer surface of the pants outer cover, to permit attachment of the finger tab 202 to the outer cover in the disposal configuration of the pants 20.

It is understood that the tab fastening component(s) 212 defining the one or more tab fastener regions 208 of the finger tab 202 can instead be a loop fastener component, with the outer surfaces of the front side panels 34 and outer cover 40 of the pants 20 being constructed to define corresponding hook fastening components. In other aspects, the tab fastening component 212 defining the tab fastener region(s) 208 and the outer surfaces of the front side panels 34 and pants outer cover 40 can include other suitable releasably fastenable fasteners without departing from the scope of this disclosure. It is also contemplated that the tab fastening component 212 defining the tab fastener region 208 can be releasably fastenable to the pants 20 (e.g., to the front side panel 34) in the wear configuration but otherwise more permanently attachable elsewhere on the pants (e.g., to the outer cover 40) in the disposal configuration of the pants. The term permanent attachment is intended herein to refer to an attachment that is generally not releasable without some damage or substantially reduced ability to reattach to the fastening component and/or the component to which the fastening component is attached.

In one alternative aspect, the tab region 206 of the finger tab 202 includes at least one gap region 218 between the attachment region 204 and the tab fastener region 208 to allow for manufacturing tolerances in preventing the tab fastening component 212 from being attached to the side panel. In other words, the gap region 218 allows the tab fastener region 208 to be free from bonding to the pants 20. Such an arrangement further reduces the opportunity for hook-on-hook interface between the tab fastening component 212 and the article fastening system 80.

In the illustrated aspect, the finger tabs 202 attach to the outer surfaces of the front side panels 34 (e.g., outer surface 30 of pants 20) in the wear configuration of the article. It is contemplated that in the wear configuration the finger tabs 202 can be configured to attach to the inner surfaces of the front side panels 34 (e.g., inner surface 28 of pants 20) and remain within the scope of this disclosure.

The attachment region 204 of each finger tab 202 is suitably attached to the respective back side panel 134 (broadly, to the respective side of the pants 20) and in the illustrated aspect is attached to the inner surface of the back side panel. It is understood, however, that the attachment region 204 can instead be attached to the outer surface of the back side panel 134. The attachment region 204, in the aspect in which the back side panel 134 overlaps the front side panel 34, is more suitably attached to the back side panel adjacent the transverse edge of the back side panel. But the attachment region 204 can instead be attached to the back side panel 134 more transversely distal from the transverse edge of the back side panel, such as when the front side panel 34 overlaps the back side panel, without departing from the scope of this disclosure.

The attachment region 204 of each finger tab 202 is suitably attached to the inner surface of the back side panel 134, such as by adhesive, thermal bonding, ultrasonic bonding, pressure bonding, or other suitable attachment technique. More suitably, an attachment face 214 (FIG. 4) of each finger tab 202 is attached to the inner surface of the back side panel 134 at the attachment region 204 of the tab. The tab region 206 of each finger tab 202 extends transversely outward of the attachment region 204 into overlapping or opposed relationship with the outer surface of the corresponding front side panel 34 so that the tab region is accessible exterior of the pants 20 in the wear configuration of the pants. It is understood, however, that the tab region 206 can instead be in opposed relationship with and releasably fastenable to the inner surface of the front side panel 34 without departing from the scope of this disclosure.

In another aspect, the tab region 206 of each finger tab 202 is suitably positioned generally longitudinally offset along the length of the side of the pants 20 (e.g., between the waist opening 50 and respective leg opening 52), and in particular at the engagement seam 66 between the front and back side panels 34, 134. More suitably, the tab region 206 has a transversely extending centerline disposed within about 8 cm from the waist opening 50 along the length of the side of the pants 20, and in particular at the engagement seam 66, and even more suitably within about 5 cm from the waist opening 50 along the length at the engagement seam 66, and still more suitably within about 2 cm from the waist opening 50 along the length at the engagement seam 66. For processing ease and aiding performance attributes associated with the finger tab 202, the finger tab 202 is positioned at least 5 mm from the waist opening 50 of the pants 20.

The tab fastener region 208 of each finger tab 202 suitably extends lengthwise of the tab, within the tab region 206 thereof, to the edges of the finger tab 202 at the tab region 206. It is understood, however, that the fastener region 208 need not extend the full length of the finger tab 202 at the tab region 206 to remain within the scope of this disclosure.

In one aspect, each finger tab 202 is suitably constructed of a base substrate 216 having a tab fastening component 212 (e.g., a hook fastening component in the illustrated aspect) attached thereto such as by adhesive bonding, thermal bonding, ultrasonic bonding, pressure bonding, or other suitable technique to define the tab fastener region 208 of the finger tab 202. In certain aspects, the base substrate 216 can be constructed such that, other than the fastener region 208, the finger tab 202 is not releasably fastenable to the pants 20, particularly at the grip region 210 (if provided) of the finger tab 202. In one particularly suitable aspect, the base substrate 216 is less stretchable (at least in the transverse direction thereof) than the pants 20 (in the transverse, or circumferential direction thereof) and more suitably the base substrate is non-stretchable so that pulling on the tab transversely of pants 20 to secure the pants 20 in their disposal configuration the pants 20 (and in particular the back side panels 134) are allowed to stretch. As an example, one suitable material from which the base substrate 216 can be constructed is a three-layer nonwoven polypropylene material known as SMS. SMS is an acronym for Spunbond-Meltblown-Spunbond, the process by which the three layers are constructed and then laminated together. One example of an SMS material is described in U.S. Pat. No. 4,041,203 to Brock et al. It should be noted, however, that other nonwovens as well as other materials including wovens, films, foam/film laminates and combinations thereof can be used to construct the finger tab 202 without departing from the scope of this disclosure.

The thickness and the basis weight of the base substrate 216 can generally vary. For example, the basis weight of the base substrate 216 can be in the range of about 20 grams per square meter ("gsm") to about 160 gsm and, in some aspects, from about 20 gsm to about 80 gsm. In one particularly suitable aspect, the basis weight of the base substrate 216 is about 60 gsm. The thickness of the base substrate 216 can suitably be in the range of about 0.165 inches (4.2 millimeters (mm)) to about 0.190 inches (4.8 mm), in some aspects from about 0.170 inches (4.3 mm) to about 0.185 inches (4.7 mm), and in other aspects, from about 0.175 inches (4.45 mm) to about 0.180 inches (4.6 mm). The thickness can be measured on an Ames model 482 Comparator using an Ames model 130 base with an auxiliary weight to provide 0.25 psi.

In particular aspects, the base substrate 216 is constructed of a material that is releasably fastenable with the article fastener component 84 of the article fastening system 80. For example, in particular aspects, the base substrate 216 is formed from a material such as acrylic, polyamide, polyethylene, polypropylene or polyester, and is formed into a "loop"-type material by methods such as warp knitting, stitch bonding or needle punching. The base substrate 216 can include any fibrous structure capable of entangling or catching hook materials, such as carded, spunbonded or other nonwoven webs or composites, including elastomeric and nonelastomeric composites. One material suitable for use as a base substrate 216 is available from Guilford Mills, Inc., Greensboro, N.C., U.S.A. under the trade designation No. 36549. Another suitable base substrate material includes a pattern un-bonded web as disclosed in co-assigned U.S. Pat. No. 5,858,515 issued Jan. 12, 1999 to Stokes, et al., which is incorporated herein by reference to the extent consistent herewith. In particular aspects, the base substrate 216 can include a "loop"-type material as just discussed but that is attached to a backing structure, and the composite is then attached to the pants 20, such as along the side edges of the front or back side panels 34, 134.

Figure 5:
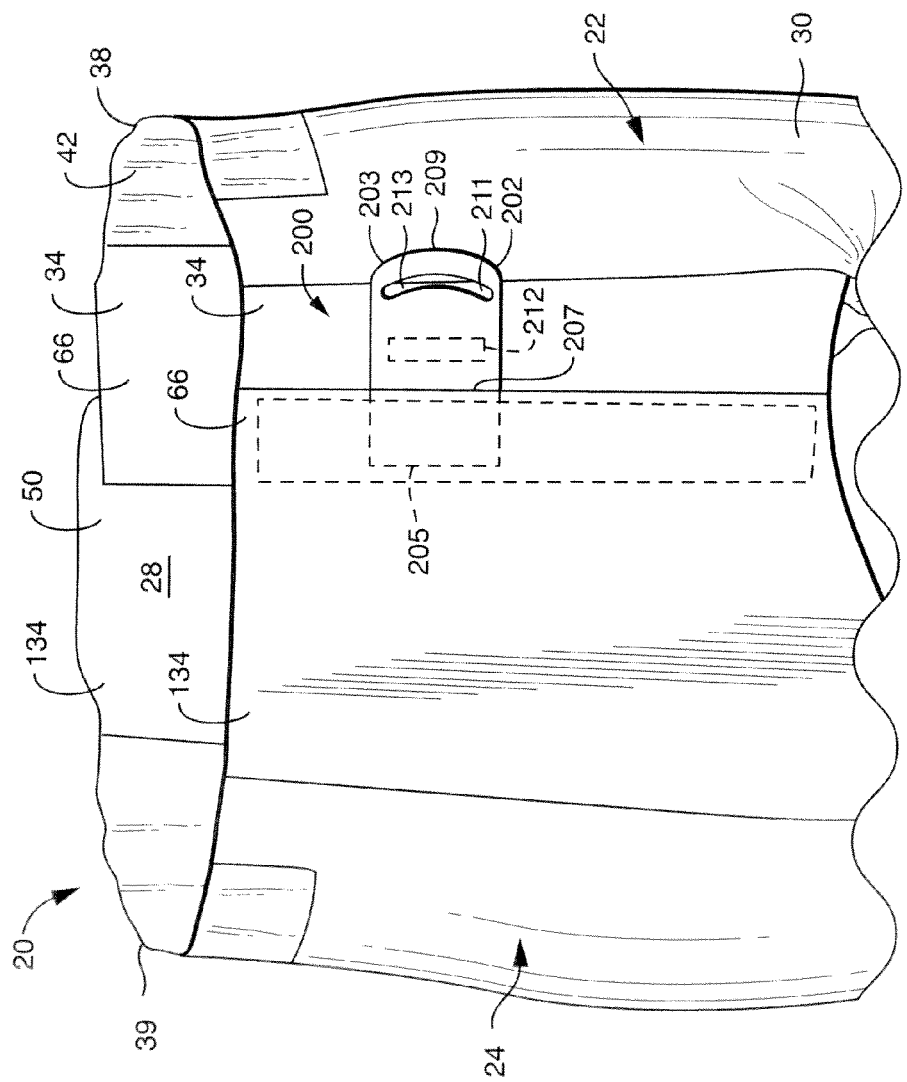
FIG. 5 is a partial perspective view of the personal wear article of FIG. 1 illustrating one aspect of the finger tab system.

In one aspect of the present disclosure illustrated primarily in FIG. 5, the first end 205 of the finger tab 202 is attached to one of the front and back side panels 34, 134 and extends generally transversely from the one of the front and back side panels 34, 134. In this aspect, the aperture 211 is a cut or slit 213 through the finger tab 202. The slit 213 is disposed between the distal point 209 and the outer edge 68 of the one of the front and back side panels 34, 134. The slit 213 is designed to allow at least one finger of a wearer or a caregiver to extend therethrough to allow the wearer or caregiver to better grip the finger tab 202 when donning the pants 20. The slit 213 can extend partially or substantially across the width of the finger tab 202. The width of the slit 213 can range from essentially zero if the slit 213 is formed by making a cut in the finger tab 202, to a wide slit 213 formed by removing a piece of the material from which the finger tab 202 is made. The slit 213 can have a width greater than 0 mm, greater than 1 mm, greater than 5 mm, greater than 10 mm, greater than 20 mm, or the slit width can vary along the length of the slit 213. The ratio of the length of the slit 213 to the width of the slit 213 can be between one and two, can be greater than 3, can be greater than 5, or can be greater than ten.

In various aspects of the present disclosure, the slit 213 can be arranged generally parallel to the tab line 207, generally perpendicular to the tab line 207, or in any other suitable orientation. The slit 213 can also be circular, elliptical, ovate, irregular, or generally arcuate in shape. In other various aspects of the present disclosure, the finger tab 202 can also include a tab fastening component 212 disposed on the finger tab 202 either between the slit 213 and the distal point 209 of the finger tab 202, or between the slit 213 and the tab line 207 of the finger tab 202.

Figure 6:
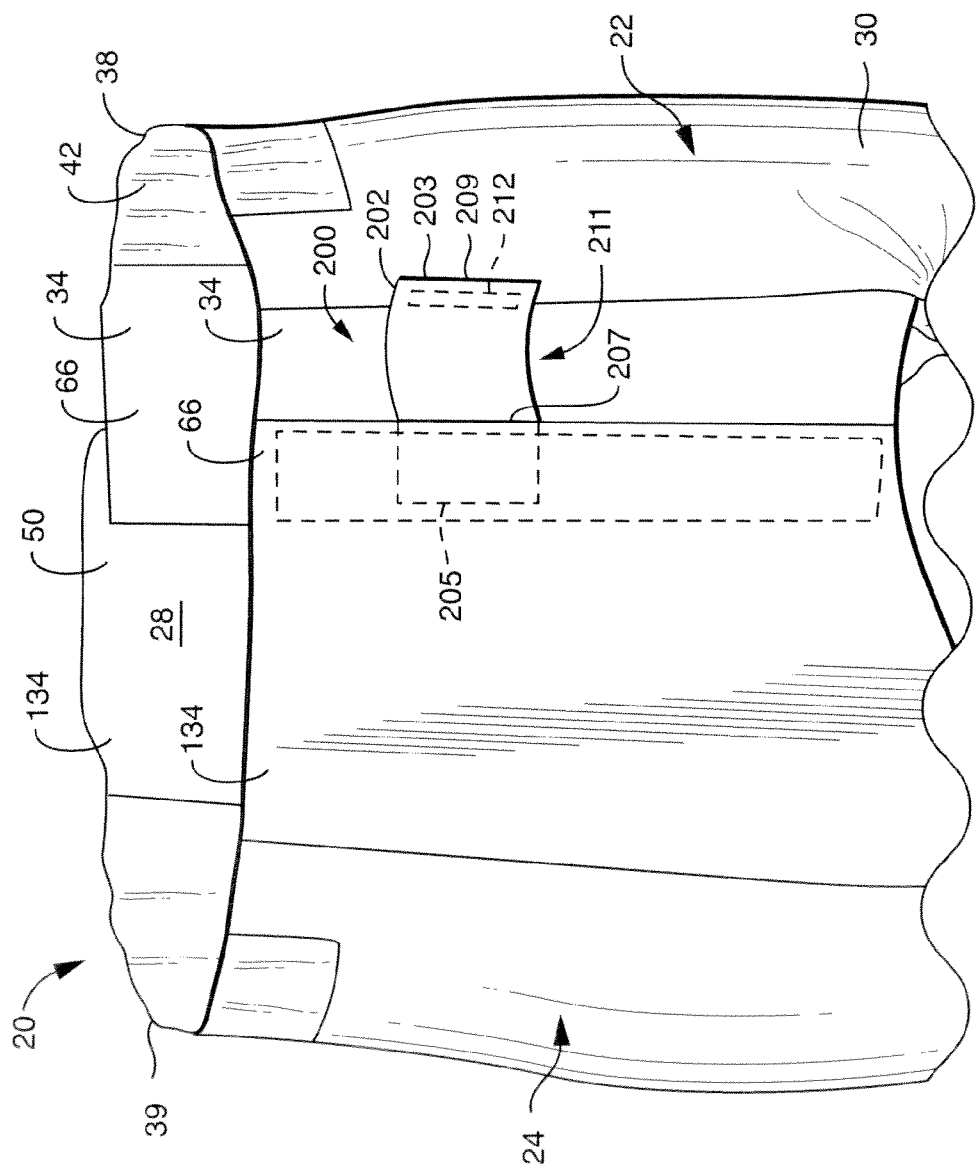
FIG. 6 is a partial perspective view of the personal wear article of FIG. 1 illustrating another aspect of the finger tab system.

In an alternative aspect of the present disclosure illustrated primarily in FIG. 6, the finger tab 202 includes a tab fastening component 212 disposed on the finger tab 202 adjacent the distal point 209. The aperture 211 is thereby formed between the finger tab 202 and one of the front and back side panels 34, 134 when the tab fastening component 212 is fastened to a front or back side panel 34, 134. The aperture 211 in this aspect is sized to allow at least one finger of a wearer or a caregiver to extend therethrough to allow the wearer or caregiver to use the finger tab 202 as a handle or strap when donning the pants 20. In this aspect, a sufficiently strong fastening between the tab fastening component 212 and the front or back side panels 34, 134 can be required to allow the finger tab 202 to be used as a handle or strap.

Figure 7:
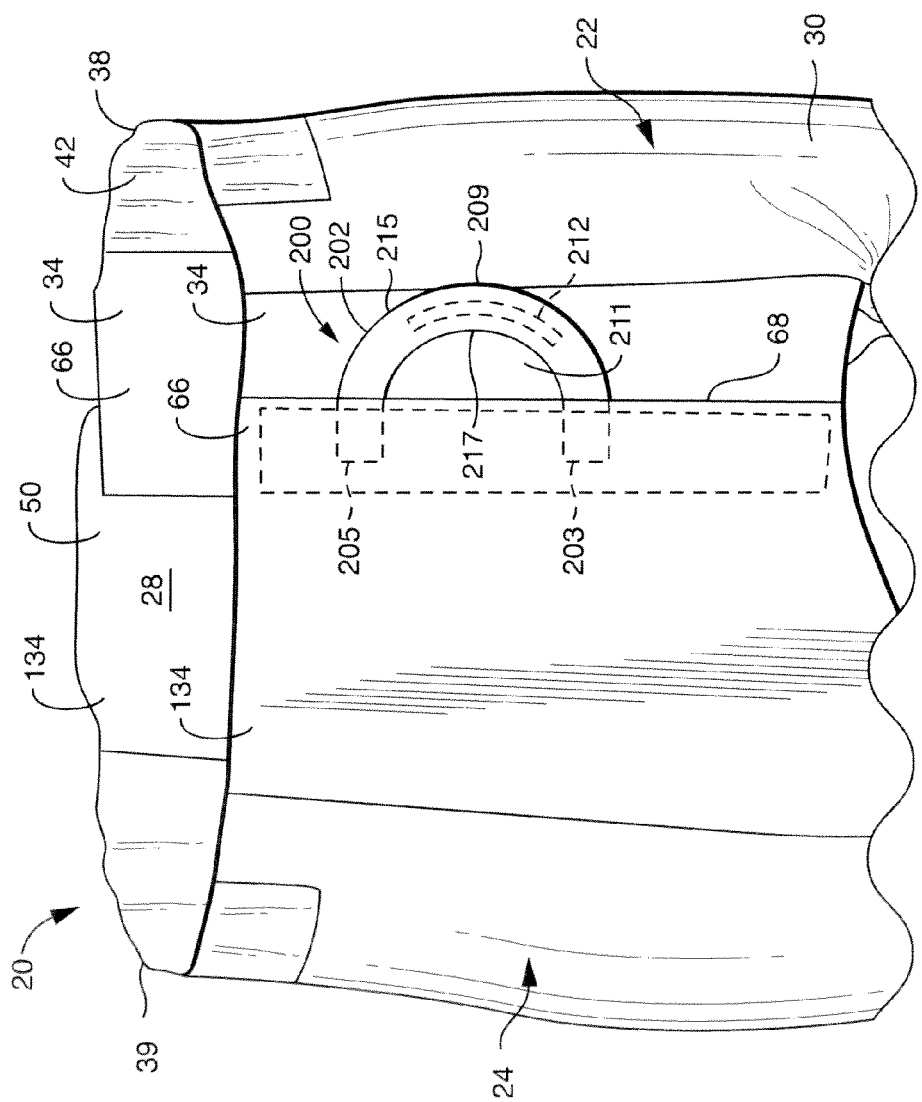
FIG. 7 is a partial perspective view of the personal wear article of FIG. 1 illustrating an alternative aspect of the finger tab system.

In another aspect of the present disclosure illustrated primarily in FIG. 7, the finger tab 202 can have first and second ends 205, 203 and an arch shape, wherein the portion of the finger tab 202 between the first and second ends 205, 203 is displaced longitudinally or transversely from a line connecting the first and second ends 203, 205. In this aspect, the finger tab 202 has a first edge 215 and a second edge 217, wherein the second edge has a concave arcuate shape. In other aspects, the first edge 215 can have a concave arcuate shape that can be parallel to the arcuate second edge 217.

In one aspect, either the first end 205 or the second end 203 of the finger tab 202 can be attached to the outer edge 68 of the one of the front and back side panels 34, 134 (not shown), or both the first and second ends 205, 203 of the finger tab 202 can be attached to the outer edge 68 of the one of the front and back side panels 34, 134, as illustrated in FIG. 7. In the latter aspect, the attachment points of the first and second ends 205, 203 are spaced apart on the outer edge 68 of the one of the front and back side panels 34, 134 such that an aperture 211 is formed between the side panel outer edge 68 and the finger tab second edge 217. The aperture 211 can have an area between 30 mm$^2$ and 2400 mm$^2$, as well as smaller ranges within that range. The aperture 211 in this aspect is sized to allow at least one finger of a wearer or a caregiver to extend therethrough to allow the wearer or caregiver to use the finger tab 202 as a handle or strap when donning the pants 20.

This arcuate finger tab 202 can have a tab fastening component 212 disposed on the finger tab 202 between the first and second ends 205, 203. This arcuate finger tab 202 can also have a tab fastening component 212 disposed on the finger tab 202 between the distal point 209 and the tab line 207. In other aspects, the tab fastening component 212 can be disposed adjacent the first or second ends 205, 203 of the finger tab 202.

Figure 8:
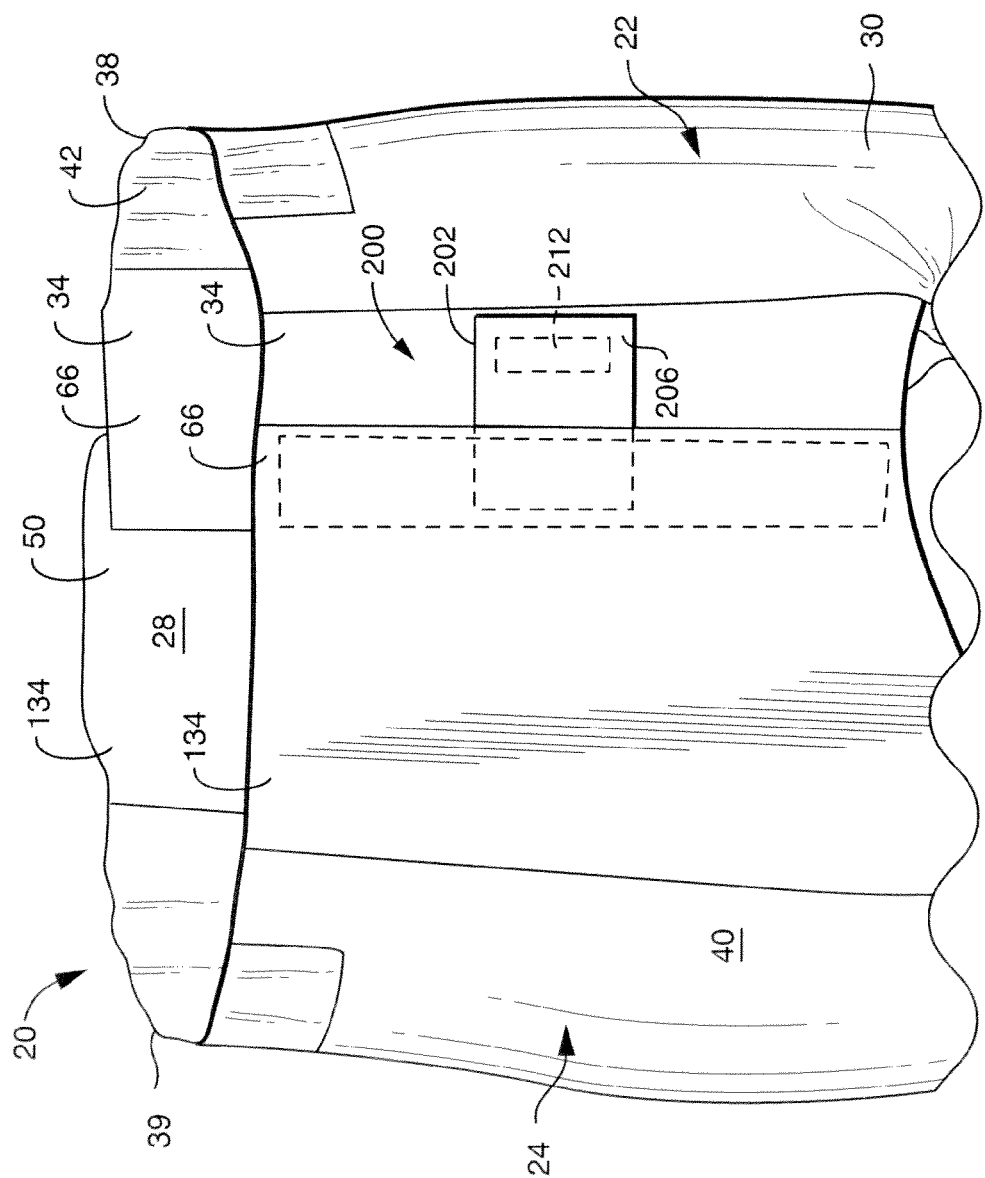
FIG. 8 is a partial perspective view of the personal wear article of FIG. 1 illustrating another alternative aspect of the finger tab system.

In an alternative aspect of the present disclosure illustrated primarily in FIG. 8, the finger tab 202 includes a rigid material configured to provide a tab stiffness that is greater than the stiffness of the front or back side panel 34, 134 to which the finger tab 202 is fastened. In another aspect, the finger tab 202 has a stiffness that is at least two times greater than that of the front or back side panel 34, 134 to which the finger tab 202 is fastened. Additional information related to stiffness is included in U.S. patent application Ser. No. 12/130,601 A2 to Faulks et al., the content of which is incorporated herein by reference to the extent it does not conflict herewith.

The rigid finger tab 202 allows a wearer or caregiver to depress the more flexible side panel material near the finger tab 202 to position a finger nail or fingertip on or under the tab to assist the wearer or caregiver in donning the article.

In one particularly suitable aspect of the present disclosure, at least the tab region 206 of the finger tab 202 and more suitably the entire finger tab 202 has a stiffness that is greater than a stiffness of the components of the pants 20 to which the finger tab 202 is fastened, such as the front and back side panels 34, 134, the outer cover 40, or the bodyside liner 42. For example, the stiffness of the finger tab 202 is at least about 10 milligrams greater than the stiffness of the side panels 34, 134, the outer cover 40, and/or the bodyside liner 42. In one suitable aspect, the finger tab 202 has a stiffness in the range of about 10 milligrams to about 10,000 milligrams and more suitably between about 10 milligrams and about 2,000 milligrams.

As used herein, stiffness is the resistance of a body to deflection or deformation (e.g., bending) when acted on by an applied force. The stiffness of the finger tab 202 and the other components of the pants 20 (e.g., the front and back side panels 34, 134, the outer cover 40, and the body side liner 42) can be determined with respect to a bending moment produced by a force that is directed perpendicular to the plane substantially defined by the length and width of the component being tested. One suitable technique for determining the stiffness values described herein is a Gurley Stiffness test, a description of which is set forth in TAPPI Standard Test T 543 om-94 (Bending Resistance of Paper (Gurley type tester)). A suitable testing apparatus is a Gurley Digital Stiffness Tester; Model 4171-D manufactured by Teledyne Gurley, a business having offices in Troy, N.Y. For purposes of the present disclosure, the stated stiffness values are intended to correspond to the values that would be generated by a "standard" sized sample using the Gurley stiffness tester. Accordingly, the scale readings from the Gurley stiffness tester are appropriately converted to the stiffness of a standard size sample, and are traditionally reported in terms of milligrams of force (mgf). Currently, a standard "Gurley unit" is equal to a stiffness value of 1 mgf, and can equivalently be employed to report the Gurley stiffness.

As a result of the increased stiffness as compared to the other components of the pants 20 (e.g., the front and back side panels 34, 134, the outer cover 40, and the body side liner 42), the finger tab 202 provides an area that is easy for a user to grasp. Thus, the finger tab 202 facilitates easy manipulation of the pants 20 between its various configurations. A user of the pants 20 can disengage the tab fastening component 212 of the finger tab 202 from the front or back side panel 34, 134 using one hand. The user can grasp the relatively stiff finger tab 202 between their thumb and forefinger and pull the finger tab 202, including the tab fastening component 212, away from the front or back side panel 34, 134 to thereby disengage the finger tab 202 from the front or back side panel 34, 134.

In addition, the greater stiffness of the finger tab 202 results in increased attachment between the tab fastening component 212 and the respective front or back side panel 34, 134 as compared to the engagement seams 66, which are formed between components having a lower stiffness. The increased stiffness of the finger tab 202 inhibits bending, folding, etc. of at least the tab fastening component 212 thereof relative to the front or back side panel 34, 134 to which the finger tab 202 is fastened, thereby reducing the potential for pop-opens.

When the pants 20 are donned by the wearer, the finger tabs 202 are disposed near the hips or slightly inward of the hips of the wearer so that the relatively stiff tabs do not compromise the comfort of the pants. That is, the finger tabs 202 are located such that the wearer can freely bend and otherwise move without any significant impediment by the finger tabs 202.

In alternate aspects of the present disclosure, the tabs described herein can be attached to any portion of a side panel or the chassis in addition to or instead of a finger tab attached to an outer edge of the front or rear side panel.

In use, the training pants 20 are constructed and pre-assembled in their wear configuration, with the article fastening system 80 releasably attaching the front and back waist regions 22, 24 (and more particularly the front and back side panels 34, 134 in the illustrated aspect). The tab fastener region 208 of each finger tab 202 is releasably fastened to the outer surface of the respective front side panel 34 to releasably attach the tab region 206 of each finger tab 202 to the pants 20 in the wear configuration of the pants 20.

When the pants 20 are to be discarded after use, the pants 20 can be slipped off of the wearer in the manner of conventional underpants, or the front and back waist regions 22, 24 can be detached from each other (e.g., by separation of the article fastening components 82, 84 of the article fastening system 80) and the pants 20 removed from the wearer. Where the front and back waist regions 22, 24 are separated to remove the pants 20, the tab fastener regions 208 of the finger tabs 202 must be detached from the front waist region (e.g., from the front side panels 34). To detach the tab fastener regions 208 of the finger tabs 202 illustrated in the aspect of FIGS. 1-4, the grip region 210 of each finger tab 202 is gripped between the thumb and forefinger and pulled away from the front side panel 34 until the tab fastener region 208 breaks free from its attachment to the front side panel 34.

When introducing elements of the present disclosure or the preferred aspect(s) thereof, the articles "a", "an", "the", and "the" are intended to mean that there are one or more of the elements. The terms "comprising," "including", and "having" are intended to be inclusive and mean that there can be additional elements other than the listed elements.

The disclosure has been described with reference to various specific and illustrative aspects and techniques. However, it should be understood that many variations and modifications can be made while remaining within the spirit and scope of the disclosure. Many alternatives, modifications and variations will be apparent to those skilled in the art in light of the foregoing description. Accordingly, this disclosure is intended to embrace all such alternatives, modifications, and variations that fall within the spirit and scope of the appended claims.

I claim:

1. An absorbent article for personal wear about a wearer's waist, the article comprising:
    a liquid permeable inner surface for facing the wearer;
    an outer surface for facing away from the wearer;
    an absorbent body disposed therebetween;
    a front waist region, a back waist region, and a crotch region extending longitudinally between and interconnecting the front and back waist regions;
    an elastomeric front side panel attached to the front waist region and an elastomeric back side panel attached to the back waist region, wherein each side panel has an attachment edge and a free edge;
    a first article fastening component coupled to one of the front and back side panels;
    a second article fastening component coupled to the other of the front and back side panels, wherein the front and back side panels are releasably fastenable to each other to define a wear configuration of the absorbent article having a waist opening and a leg opening spaced from the waist opening, wherein the front and back side panels each extend from the waist opening to the leg opening; and
    a finger tab system including a finger tab having first and second ends, a tab fastening component, and a distal point, the first end of the finger tab being attached to the free edge of one of the front and back side panels, and a tab line where the finger tab intersects the free edge of the one of the front and back side panels, wherein the finger tab system includes an aperture disposed between the distal point of the finger tab and the tab line and wherein the aperture is a slit through the finger tab, and wherein the tab fastening component is disposed on the finger tab between the slit and the tab line.

2. An absorbent article for personal wear about a wearer's waist, the article comprising:
    a liquid permeable inner surface for facing the wearer;
    an outer surface for facing away from the wearer;
    an absorbent body disposed therebetween;
    a front waist region, a back waist region, and a crotch region extending longitudinally between and interconnecting the front and back waist regions;
    an elastomeric front side panel attached to the front waist region and an elastomeric back side panel attached to the back waist region, wherein each side panel has an attachment edge and a free edge;
    a first article fastening component coupled to one of the front and back side panels;
    a second article fastening component coupled to the other of the front and back side panels, wherein the front and back side panels are releasably fastenable to each other to define a wear configuration of the absorbent article having a waist opening and a leg opening spaced from the waist opening, wherein the front and back side panels each extend from the waist opening to the leg opening; and
    a finger tab system including a finger tab having first and second ends and a distal point, the first end of the finger tab being attached to the free edge of one of the front and back side panels, and a tab line where the finger tab intersects the free edge of the one of the front and back side panels, wherein the finger tab system includes an aperture disposed between the distal point of the finger tab and the tab line and wherein the aperture is a slit through the finger tab, further comprising a tab fastening component disposed on the finger tab between the slit and the distal point of the finger tab.

3. The article of claim 1, wherein the slit is arranged generally parallel to the tab line.

4. The article of claim 1, wherein the slit is arranged generally perpendicular to the tab line.

5. The article of claim 1, wherein the slit is generally arcuate.

6. The article of claim 1, wherein the slit has a slit length and a slit width, and wherein the ratio of the slit length to the slit width is greater than three.

7. The article of claim 1, wherein the slit has a slit length and a slit width, and wherein the ratio of the slit length to the slit width is greater than five.

8. The article of claim 1, wherein the slit has a slit length and a slit width, and wherein the ratio of the slit length to the slit width is greater than ten.

9. The article of claim 1, wherein the slit has a slit length and a slit width, and wherein the ratio of the slit length to the slit width is between one and two.

10. An absorbent article for personal wear about a wearer's waist, the article comprising:

a liquid permeable inner surface for facing the wearer;

an outer surface for facing away from the wearer;

an absorbent body disposed therebetween;

a front waist region, a back waist region, and a crotch region extending longitudinally between and interconnecting the front and back waist regions;

an elastomeric front side panel attached to the front waist region and an elastomeric back side panel attached to the back waist region, wherein each side panel has an attachment edge and a free edge;

a first article fastening component coupled to one of the front and back side panels;

a second article fastening component coupled to the other of the front and back side panels, wherein the front and back side panels are releasably fastenable to each other to define a wear configuration of the absorbent article having a waist opening and a leg opening spaced from the waist opening, wherein the front and back side panels each extend from the waist opening to the leg opening; and a finger tab system including a finger tab having first and second ends and a distal point, the first end of the finger tab being attached to the free edge of one of the front and back side panels, and a tab line where the finger tab intersects the free edge of the one of the front and back side panels, wherein the finger tab system includes an aperture disposed between the distal point of the finger tab and the tab line further comprising a tab fastening component disposed on the finger tab adjacent the distal point, wherein the aperture is disposed between the tab fastening component and one of the front and back side panels.

11. The article of claim 1, wherein the finger tab has first and second edges, and wherein the second edge is a concave arcuate second edge.

12. The article of claim 11, wherein the second end of the finger tab is attached to the free edge of the one of the front and back side panels at a point spaced apart from the first end such that the aperture is formed between the concave arcuate second edge and the tab line.

13. The article of claim 12, wherein the aperture has an area between 30 mm$^2$ and 2400 mm$^2$.

14. The article of claim 11, further comprising a tab fastening component disposed on the finger tab between the distal point and the tab line.

15. The article of claim 11, wherein the first edge is arcuate and parallel to the finger tab second edge.

* * * * *